United States Patent [19]

Ratfisch

[11] Patent Number: 4,981,652
[45] Date of Patent: Jan. 1, 1991

[54] APPARATUS FOR CONTINUOUSLY MEASURING THE HYDROCARBON CONCENTRATION IN A GAS FLOW

[75] Inventor: Werner Ratfisch, Munich, Fed. Rep. of Germany

[73] Assignee: Ratfisch Instrument, Munich, Fed. Rep. of Germany

[21] Appl. No.: 322,090

[22] Filed: Mar. 10, 1989

[30] Foreign Application Priority Data

Mar. 17, 1988 [DE] Fed. Rep. of Germany ....... 3808982

[51] Int. Cl.$^5$ ..................... G01N 21/00; G01N 30/00; G01N 35/00
[52] U.S. Cl. ......................................... 422/54; 422/52; 422/90; 422/93; 422/94; 422/98; 436/153; 436/154; 436/158; 436/139; 324/459; 324/464; 73/23.31

[58] Field of Search ........................ 422/52, 54, 90, 93, 422/94, 98; 436/153, 154, 158, 52, 53, 139; 324/459, 464; 73/23

[56] References Cited

U.S. PATENT DOCUMENTS 4,341,108 7/1982 Warncke et al. ........................ 73/23

Primary Examiner—Robert J. Warden
Assistant Examiner—David Redding
Attorney, Agent, or Firm—Henry M. Feiereisen

[57] ABSTRACT

An apparatus for continuously measuring the hydrocarbon concentration in a gas flow includes at least one flame ionization detector with a combustion chamber housing electrodes between which a current flows due to ionization in the area of a burner flame. The combustion chamber of the flame ionization detector is connected to a suction pump in form of a venturi tube for applying an underpressure in the combustion chamber so as to allow especially sample gas but also burner gas and oxidizer to be drawn into the combustion chamber.

7 Claims, 1 Drawing Sheet

APPARATUS FOR CONTINUOUSLY MEASURING THE HYDROCARBON CONCENTRATION IN A GAS FLOW

BACKGROUND OF THE INVENTION

The present invention refers to an apparatus for continuously measuring the hydrocarbon concentration in a gas flow.

Hydrocarbon concentrations in a gas flow can be measured by using a flame ionization detector with a combustion chamber in which burner gas such as hydrogen, an oxidizer such as synthetic air and sample gas to be tested is introduced. The flame ionization detector includes a burner with electrodes in vicinity of the burner flame. A direct voltage is applied to the electrodes, and the ionization in the area of the burner flame results in a current flow between the electrodes which is a function of the portion of hydrocarbons in the sample gas to be tested and is about directly proportional to the number of hydrocarbon atoms introduced into the flame per unit of time.

The principle of flame ionization and the use of flame ionization detectors are known and their application is wide spread, such as e.g. for exhaust gas measurement in motor vehicles, in the chemical and petrochemical industry, electrical industry, in the area of coating plants e.g. for the furniture industry during coating of chip boards with veneer, or in the packaging industry when webs of carrier material should be laminated at one side or at both sides with a coating of plastic material.

All known methods and apparatuses are characterized by pumping the sample gas, the burner gas and the oxidizer into the combustion chamber of the flame ionization detector at overpressure. This is disadvantageous for a variety of reasons such as safety reasons or inaccuracy of the measurement.

SUMMARY OF THE INVENTION

It is thus an object of the present invention to provide an improved method of and improved apparatus for continuously measuring the hydrocarbon concentration in a gas flow obviating the afore-stated drawbacks.

This object and others which will become apparent hereinafter are attained in accordance with the present invention by applying an underpressure within the combustion chamber of the flame ionization detector for drawing sample gas into the combustion chamber.

Preferably, the underpressure is attained by linking the combustion chamber to a suction pump (vacuum pump) by which a predetermined underpressure is created in the combustion chamber for allowing sample gas and in addition burner gas and oxidizer to be drawn into the combustion chamber. Preferably, the suction pump is a venturi tube through which compressed air flows and which may be connected to the atmosphere for discharging exhaust gases formed in the combustion chamber. The pressure created in the combustion chamber by the venturi tube is suitably in the range of about 20–400 mm Hg, preferably in the range of about 25–380 mm Hg.

Through linking the flame ionization detector with a suction pump in order to draw sample gas as well as burner gas and oxidizer into the combustion chamber, numerous advantages are achieved. For example, the absorption/desorption is considerably reduced in all sample gas conduits. Since the combustion chamber is subjected to underpressure and thus to a pressure below atmospheric pressure, solvent with higher boiling point stay vaporized. Moreover, the measuring sensitivity is increased and contamination of the combustion chamber is reduced. The use of force pumps and back pressure regulators which frequently fail is not required so that the operation is safer and more reliable. Also, the noise level is reduced because there is no necessity of using diaphragm pumps. Finally, the sample gas in the flame ionization detector can be subjected to higher temperatures.

The sample gas to be tested is supplied to the combustion chamber via a capillary tube at a rate of e.g. only about 20–30 cm$^3$/min. Therefore, according to a further feature of the present invention, it is proposed to provide a bypass system by which a portion of the sample gas is released directly to the atmosphere. The bypass system includes a bypass venturi tube connected parallel to the main venturi tube which is linked to the combustion chamber. Suitably, the absolute pressure generated by the bypass venturi tube is higher than the absolute pressure generated by the main venturi tube, preferably by at least 20–40 mm Hg, and thus may be in the range of about 50–425 mm Hg.

BRIEF DESCRIPTION OF THE DRAWING

The above and other objects, features and advantages of the present invention will now be described in more detail with reference to the accompanying drawing in which:

The sole figure is a schematic illustration of one embodiment of a hydrocarbon concentration measuring system for a gas flow in accordance with the present invention.

DETAILED DESCRIPTION OF A PREFERRED EMBODIMENT

Figure 1:
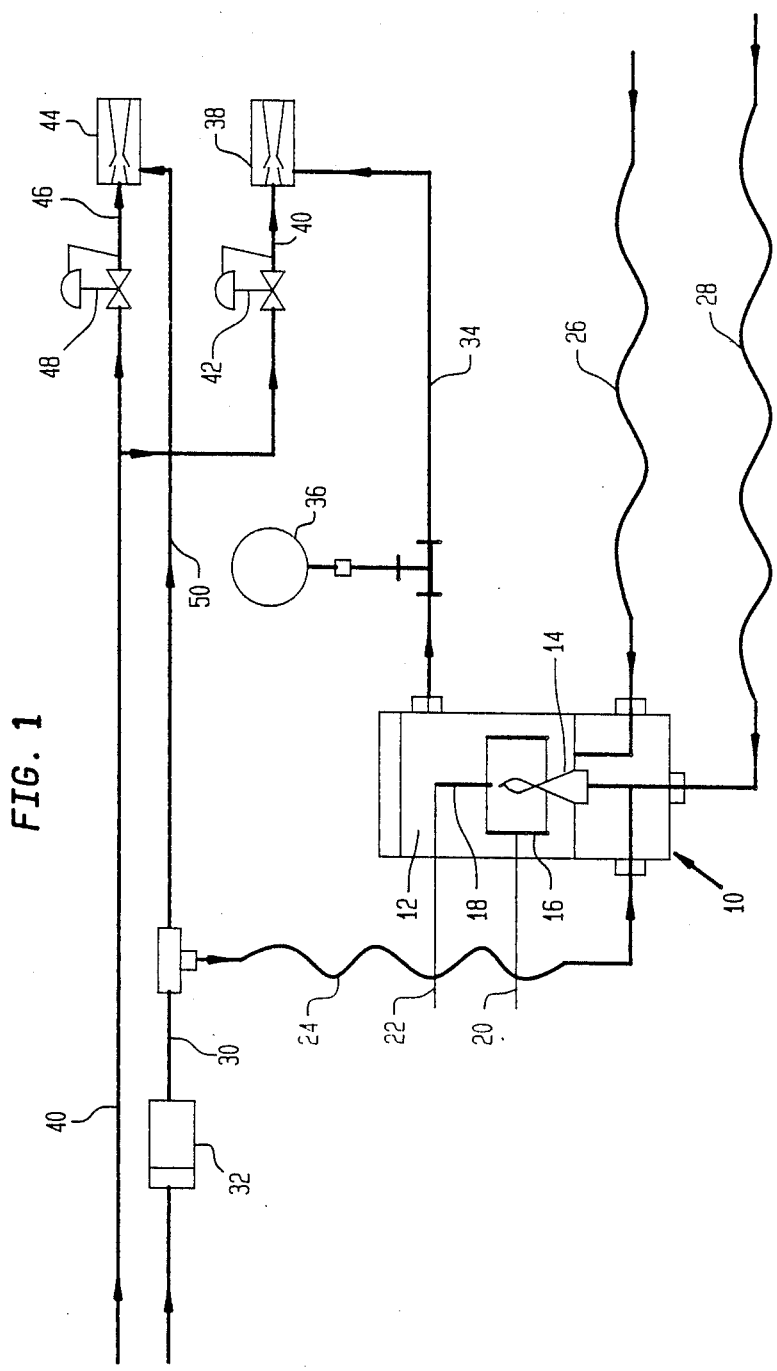

In the drawing, there is shown a schematic illustration of one embodiment of hydrocarbon concentration measuring system for a gas flow in accordance with the present invention and including a flame ionization detector generally designated by reference numeral 10. The flame ionization detector 10 defines a combustion chamber 12 which accommodates a burner 14. Cooperating with the burner 14 and arranged within the combustion chamber 12 in vicinity of the burner flame are electrodes such as for example an annular electrode 16 and a stick electrode 18. Lines 20, 22 connect the electrodes 16, 18 to a not shown electric power supply to apply direct voltage.

Sample gas is withdrawn from a suitable withdrawal point and guided through a conduit 30 via a filter 32. A capillary tube 24 is connected to the conduit 30 and supplies the sample gas to the burner 14. Burner gas such as e.g. hydrogen is fed via a capillary tube 26, and oxidizer such as e.g. synthetic air is introduced into the combustion chamber 12 through a capillary tube 28.

Ionization in the area of the burner flame results in a flow of current between the electrodes 16, 18 which current is a function of the portion of hydrocarbons in the sample gas. Burners, such as burner 14 permit a linear measurement of concentrations of few ppm up to a high percentage range. Their response time is below a second, and the current which flows between the electrodes is approximately directly proportional to the number of hydrocarbons atoms introduced into the flame per unit of time.

It should be noted that the principle of flame ionization and the operation and function of flame ionization detectors are generally known and thus requires no detailed description thereof.

As is further shown in the figure, the combustion chamber 12 is connected via a conduit 34 to a main venturi tube or nozzle 38. Suitably, the conduit 34 enters the combustion chamber 12 at a distance to the burner flame. Connected to the conduit 34 upstream between the combustion chamber 12 and the venturi tube 38 is a manometer 36 for measuring the pressure in the conduit 34. The venturi tube 38 is operated with compressed air, preferably dry compressed air which is supplied to the venturi tube 38 through conduit 40. For controlling the pressure, a pressure regulator 42 is provided in the conduit 40 at an upstream section before the venturi tube 38.

After having described the individual parts of a system for measuring the hydrocarbon concentration in a gas flow, its mode of operation will now be set forth in detail.

Compressed air is supplied through the conduit 40 to the venturi tube 38, with the pressure of the compressed air being adjustable by means of the pressure regulator 42. The venturi tube 38 thus generates in the combustion chamber 12 via conduit 34 an underpressure, the level of which is adjustable by controlling the operational pressure of the venturi tube 38 with the pressure regulator 42. The underpressure in the combustion chamber 12 of the flame ionization detector 10 causes gases to be drawn through the capillary tubes 24, 26, 28 and into the interior of the combustion chamber 12. Thus, by applying a controllable underpressure in the combustion chamber 12, a desired predetermined amount of sample gas can be drawn through the capillary tube 24.

The pressure in conduit 34 and thus the underpressure in the combustion chamber 12 is measured by the manometer 36. Exhaust gases generated in the combustion chamber 12 are discharged through the conduit 34 and released via the venturi tube 38 e.g. into the atmosphere.

In many instances, the capillary tube 24 is dimensioned for the supply of sample gas into and through the combustion chamber 12 at a rate of only about 20–30cm$^3$/min. Therefore, the provision of a bypass is suitable in order to allow portions of the sample gas to be discharged directly into the atmosphere.

In accordance with the present invention, the bypass includes a bypass venturi tube 44 which extends parallel to the venturi tube 38 and is connected to a branch line 46 branching off conduit 40. Interposed in the branch line 46 at an upstream section before the bypass venturi tube 44 is a further pressure regulator 48 to permit control of the pressure in the branch line 46. The bypass venturi tube 44 is supplied with compressed air from conduit 40 via branch line 46. As is further shown in the figure, the bypass venturi tube 44 is also connected to a branch line 50 which branches off conduit 30.

Thus, sample gas is not only drawn from conduit 30 into the capillary tube 24 by means of the main venturi tube 38 but portions thereof may be drawn into branch line 50 by means of the venturi tube 44 and e.g. directly released into the atmosphere.

It will be readily recognized that the absolute pressure in the bypass venturi tube 44 should be higher than the absolute pressure in the venturi tube 38 so that the underpressure generated by the venturi tube 38 exceeds the underpressure created by the venturi tube 44. The difference of both underpressures or both absolute pressures can be controlled through suitably setting the pressure regulators 42, 48.

Suitably, the pressure generated by the venturi tube 38 within the combustion chamber 38 may be in the range of 20–400 mm Hg, preferably in the range of 25–380 mm Hg, while the pressure generated by the bypass venturi tube 44 should be higher by at least about 20–40 mm Hg i.e. the generated pressure should be approximately between 50–425 mm Hg.

It will be appreciated that the present invention should not be limited to its application with one flame ionization detector; rather, the present invention is applicable also for a number of flame ionization detectors which are e.g. connected parallel or operated parallel. In addition, suction devices or suction pumps other than venturi tubes illustrated herein for applying an underpressure in the combustion chamber of the flame ionization detector should be considered within the scope of the invention.

While the invention has been illustrated and described as embodied in an apparatus for continuously measuring the hydrocarbon concentration in a gas flow, it is not intended to be limited to the details shown since various modifications and structural changes may be made without departing in any way from the spirit of the present invention.

What is claimed as new and desired to be protected by Letters Patent is set forth in the appended claims:

I claim:

1. In an apparatus for continuously measuring the hydrocarbon concentration in a gas flow, including at least one flame ionization detector having a combustion chamber housing a burner flame and in the area of the burner flame electrodes to which direct voltage is applied and between which a current flows upon burning of the sample gas which current is a function of the portion of hydrocarbons in the gas flow, the improvement comprising:

capillary means with an inlet and an outlet in communication with the flame ionization detector for adjusting the amount of sample gas to be supplied to the flame ionization detector;

first suction means connected to the combustion chamber for applying an underpressure within the combustion chamber of the flame ionization detector to allow sample gas to be drawn through said capillary means and into the combustion chamber; and second suction means communicating with the inlet of said capillary means and arranged parallel to said first suction means for diverting an excess amount of withdrawn sample gas and releasing it directly to the atmosphere.

2. Apparatus as defined in claim 1 wherein said first suction means includes a venturi tube with compressed air flowing therethrough.

3. Apparatus as defined in claim 1 wherein said venturi tube is connected to the atmosphere to allow exhaust gas to be discharged.

4. Apparatus as defined in claim 1 wherein said bypass means includes a second suction venturi tube with compressed air flowing therethrough.

5. Apparatus as defined in claim 1 and further comprising a source for burner gas and a source for oxidizer, said first suction means being suitably connected to said burner gas source and said oxidizer source for allowing burner gas and oxidizer to be drawn into said combustion chamber by said first suction means.

6. Apparatus as defined in claim 1, and further comprising a first pressure regulator cooperating with said first suction mean for regulating the underpressure generated by said first suction means, and a second pressure regulator cooperating with said second suction means for regulating the underpressure generated by said second suction means.

7. Apparatus as defined in claim 6 wherein said first suction means generates an absolute pressure and said second suction means generates an absolute pressure, said absolute pressure generated by said first suction means being lower than said absolute pressure generated by said second suction means.

* * * * *

UNITED STATES PATENT AND TRADEMARK OFFICE
CERTIFICATE OF CORRECTION

PATENT NO. : 4,981,652
DATED : January 1, 1991
INVENTOR(S) : WERNER RATFISCH

It is certified that error appears in the above-identified patent and that said Letters Patent is hereby corrected as shown below:

COLUMN 4;

Claim 4, line 1, delete "by-"
Claim 4, line 2, delete "pass means includes a second suction" and substitute therefor -- second suction means includes a bypass --.

Signed and Sealed this

Twenty-first Day of July, 1992

Attest:

DOUGLAS B. COMER

*Attesting Officer*   *Acting Commissioner of Patents and Trademarks*